United States Patent
Doerner et al.

(10) Patent No.: US 6,252,139 B1
(45) Date of Patent: Jun. 26, 2001

(54) METHOD OF INCREASING GROWTH AND YIELD IN PLANTS

(75) Inventors: Peter W. Doerner; Christopher J. Lamb, both of San Diego, CA (US)

(73) Assignee: The Salk Institute for Biological Studies, La Jolla, CA (US)

(*) Notice: Subject to any disclaimer, the term of this patent is extended or adjusted under 35 U.S.C. 154(b) by 0 days.

(21) Appl. No.: 08/683,242

(22) Filed: Jul. 18, 1996

(51) Int. Cl.⁷ ............................... A01H 5/00; C12N 15/82
(52) U.S. Cl. ........................... 800/290; 435/419; 435/468
(58) Field of Search ...................................... 800/205, 250, 800/290; 536/23.6, 24.1; 435/172.3, 240.4, 320.1, 419

(56) References Cited

U.S. PATENT DOCUMENTS 5,750,862 * 5/1998 John ...................................... 800/205

OTHER PUBLICATIONS

Ito et al. (1994) Merislem,–specific gene expression directed by the promoter of the S–phase–specific gene, cyc07, In transgenic arabidopsis. Plant Molecular Biology, 24:863–878.
Wong et al. (1996) Differential activation of the primary auxin response genes, PS–IA4/5 and PS–IAA6 during early plant development. The Plant Journal. 9(5): 587–599.
Hemerly et al. Proc. Natl. Acad. Sci. USA, vol. 89, pp. 3295–3299, Apr. 1992.*
Hata et al. The EMBO Journal. vol. 10, No. 9, pp. 2681–2688,1991.*
Ferreia et al. Plant Molecular Biology 26: 1289–1303, 1994.*
Hemerly et al. The EMBO Journal 14 (15): 3925–39–36, 1995.*
Napoli et al. Introduction of a Chimeric Chalcone Synthase Gene into Petunia Results in Reversible Co–Suppression of Homologous Genes in tran. The Plant Cell, vol. 2, 279–289, Apr. 1990.*
Hemerly et al. Genes regulating the plant cell cycle: Isolation of a mitotic–like cyclin from Arabidopsis thaliana. Proc. Natl. Acad. Sci. USA, vol. 89, pp. 3295–3299, Apr. 1992.*
Ferreira et al. Control of cell proliferation during plant development. Plant Molecular Biology 26: 1289–1303, 1994.*
Hata et al. Isolation and characterization of cDNA clones for plant cyclins. The EMBO Journal vol. 10 No. 9, pp. 2681–2688, 1991.*

Kawaoka et al. Growth–Stimulation of Tobacco Plant Introduced the Horseradish Peroxidase Gene prxC1a. Journal of Fermentation and Bioengineering. vol. 78, No. 1, 49–53, 1994.*
Hemerly, et al., "Dominant negative mutants of the Cdc2 kinase uncouple cell division from iterative plant development," *The EMBO Journal* 14 (15):3925–3936 (1995).
Dooner et al., "Genetic and Development Control of Anthocyanin Biosynethesis", *Annu. Rev. Genet.*, 1991 25:173–99.
Chandler et al., "Two Regulatory Genes of the Maize Anthocyanin Pathway Are Homologous: Isolation of B Utilizing R Genomic Sequences", *The Plant Cell*, vol. 1, 1175–1183, Dec. 1989.
Koff et al., "Human Cyclin E, a New Cyclin That Interacts with Two Members of the CDC2 Gene Family", *Cell*, vol. 66, 1217–1228, Sep. 20, 1991.
Holton et al., "Genetics and Biochemistry of Anthocyanin Biosynthesis", *The Plant Cell*, vol. 7, 1071–1083, Jul. 1995.
Leopold et al., "An Evolutionary Conserved Cyclin Homolog from Drosophila Rescues Yeast Deficient in G1 Cyclins", *Cell*, vol. 66, 1207–1216, Sep. 20, 1991.
Lew et al., "Isolation of Three Novel Human Cyclins by Rescue of G1 Cyclin (Cln) Function in Yeast", *Cell*, vol. 66, 1197–1206, Sep. 20, 1991.
Schwob et al., *CLB5* and *CLB6*, a new pair of B cyclin involved in DNA replication in *Saccharomyces cerevisiae, Genes and Development*, &;1160–1175 1993.
Hrabak et al., "Characterization of eight new members of the calmodulin–like domain protein kinase gene family from *Arabidopsis thaliana*", *Plant Molecular Biology*, 31:405–412, 1996.
Renaudin et al., "Plant cyclins: a unified nomenclature for plant A–, B–and D–type cyclins based on sequence orgniazation", *Plant Molecular Biology*, 1996 32:1003–1018.
Lloyd AM et al., "Arabidopsis and Nicotiana anthocyanin production activated by maize regulators R and C1", *Science*, 1992 258:1773–1775.
Peter W. Doerner, *Cell Cycle Regulation in Plants*, Plant Physiol. vol. 106:823–827, 1994.

* cited by examiner

*Primary Examiner*—Elizabeth F. McElwain
*Assistant Examiner*—Cynthia Collins
(74) *Attorney, Agent, or Firm*—Knobbe, Martens, Olson, Bear LLP

(57) ABSTRACT

The invention provides a method of producing a genetically modified plant characterized as having increased growth and yield as compared to a corresponding wild-type plant comprising increasing the level of cyclin expression in the plant. Genetically modified plants characterized as having increased growth and yield are also provided.

9 Claims, 4 Drawing Sheets

METHOD OF INCREASING GROWTH AND YIELD IN PLANTS

FIELD OF THE INVENTION

The present invention relates generally to plant genetic engineering, and specifically to a method for producing genetically engineered plants characterized as having increased growth and yield.

BACKGROUND OF THE INVENTION

For each plant species, there exists a wide discrepancy in plant growth due to environmental conditions. Under most conditions, the maximum growth potential of a plant is not realized. Plant breeding has demonstrated that a plant's resources can be redirected to individual organs to enhance growth.

Genetic engineering of plants, which entails the isolation and manipulation of genetic material, e.g., DNA or RNA, and the subsequent introduction of that material into a plant or plant cells, has changed plant breeding and agriculture considerably over recent years. Increased crop food values, higher yields, feed value, reduced production costs, pest resistance, stress tolerance, drought resistance, the production of pharmaceuticals, chemicals and biological molecules as well as other beneficial traits are all potentially achievable through genetic engineering techniques.

The ability to manipulate gene expression provides a means of producing new characteristics in transformed plants. For example, the ability to increase the size of a plant's root system would permit increased nutrient assimilation from the soil. Moreover, the ability to increase leaf growth would increase the capacity of a plant to assimilate solar energy. Obviously, the ability to control the growth of an entire plant, or specific target organs thereof would be very desirable.

SUMMARY OF THE INVENTION

The present invention is based on the discovery that increased growth and yield in plants can be achieved by elevating the level of cyclin expression.

In a first embodiment, the invention provides a method of producing a genetically modified plant characterized as having increased growth and yield as compared to a corresponding wild-type plant. The method comprises contacting plant cells with nucleic acid encoding a cyclin protein, wherein the nucleic acid is operably associated with a regulatory sequence, to obtain transformed plant cells; producing plants from the transformed plant cells; and selecting a plant exhibiting said increased yield. The cyclin-encoding nucleic acid preferably encodes the cyclin cyc1aAt.

In another embodiment, the invention provides a method of producing a plant characterized as having increased yield, the method comprising contacting a plant with an agent which elevates cyclin expression above cyclin expression in a plant not contacted with the agent. The agent may be a transcription factor or a chemical agent which induces an endogenous cyclin promoter or other chemically inducible promoter driving expression as the cyclin transgene.

The invention also provides plants, plant tissue and seeds produced by the methods of the invention.

DESCRIPTION OF THE PREFERRED EMBODIMENTS

Figure 1A:
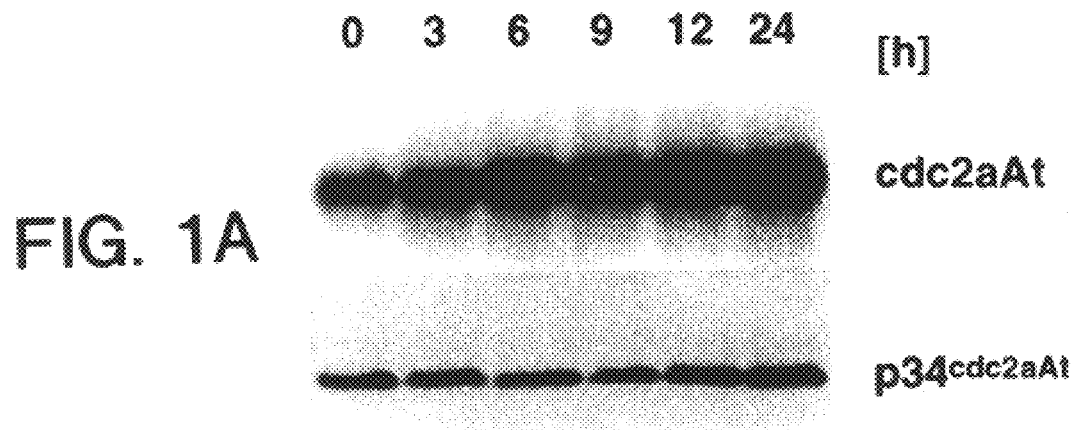
FIG. 1 shows steady state levels of cdc2aAt mRNA and p34 protein, panel a; cyc1aAt mRNA during IAA induction of lateral root meristems, panel b; cyc1aAt mRNA in selected non-induced transgenic lines, panel c; normalized transcript levels relative to wild-type are indicated. Col-0, wild-type; 1A2, 2A5, 4A3, 11A1: T2 homozygous; 6A, 7A, 8: T1 heterozygous transgenic lines.

The present invention provides methods for increasing the yield of a plant, such as a agricultural crop, by elevating the cyclin expression level in the plant. Increased cyclin expression in plant cells competent to divide results in increased plant growth.

In a preferred embodiment, the invention provides a method for producing a genetically modified plant characterized as having increased yield as compared to a plant which has not been genetically modified (e.g., a wild-type plant). The method comprises contacting plant cells with nucleic acid encoding a cyclin protein, wherein the nucleic acid is operably associated with a regulatory sequence to obtain transformed plant cells; producing plants from the transformed plant cells; and thereafter selecting a plant exhibiting increased growth and yield.

As used herein, the term "yield" or "plant yield" refers to increased crop growth, and/or increased biomass. In one embodiment, increased yield results from increased growth rate and increased root size. In another embodiment, increased yield is derived from shoot growth. In still another embodiment, increased yield is derived from fruit growth.

The term "genetic modification" as used herein refers to the introduction of one or more exogenous nucleic acid sequences, e.g., cyclin encoding sequences, as well as regulatory sequences, into one or more plant cells, which can generate whole, sexually competent, viable plants. The term "genetically modified" as used herein refers to a plant which has been generated through the aforementioned process. Genetically modified plants of the invention are capable of self-pollinating or cross-pollinating with other plants of the same species so that the foreign gene, carried in the germ line, can be inserted into or bred into agriculturally useful plant varieties. The term "plant cell" as used herein refers to protoplasts, gamete producing cells, and cells which regenerate into whole plants.

As used herein, the term "plant" refers to either a whole plant, a plant part, a plant cell, or a group of plant cells, such as plant tissue or plant seed. Plantlets are also included within the meaning of "plant". Plants included in the invention are any plants amenable to transformation techniques, including gymnosperms and angiosperms, both monocotyledons and dicotyledons.

Examples of monocotyledonous angiosperms include, but are not limited to, asparagus, field and sweet corn, barley, wheat, rice, sorghum, onion, pearl millet, rye and oats and other cereal grains. Examples of dicotyledonous angiosperms include, but are not limited to tomato, tobacco, cotton, rapeseed, field beans, soybeans, peppers, lettuce, peas, alfalfa, clover, cole crops or *Brassica oleracea* (e.g., cabbage, broccoli, cauliflower, brussel sprouts), radish, carrot, beets, eggplant, spinach, cucumber, squash, melons, cantaloupe, sunflowers and various ornamentals. Examples of woody species include poplar, pine, sequoia, cedar, oak, etc.

The term "exogeneous nucleic acid sequence" as used herein refers to a nucleic acid foreign to the recipient plant host or, native to the host if the native nucleic acid is substantially modified from its original form. For example, the term includes a nucleic acid originating in the host species, where such sequence is operably linked to a promoter that differs from the natural or wild-type promoter. In the broad method of the invention, at least one nucleic acid sequence encoding cyclin is operably linked with a promoter. It may be desirable to introduce more than one copy of cyclin polynucleotide into a plant for enhanced cyclin expression. For example, multiple copies of a cyclin polynucleotide would have the effect of increasing production of cyclin even further in the plant.

The term "regulatory sequence" as used herein refers to a nucleic acid sequence capable of controlling the transcription of an operably associated gene. Therefore, placing a gene under the regulatory control of a promoter or a regulatory element means positioning the gene such that the expression of the gene is controlled by the regulatory sequence(s). In general, promoters are found positioned 5' (upstream) of the genes that they control. Thus, in the construction of promoter gene combinations, the promoter is preferably positioned upstream of the gene and at a distance from the transcription start site that approximates the distance between the promoter and the gene it controls in the natural setting. As is known in the art, some variation in this distance can be tolerated without loss of promoter function. Similarly, the preferred positioning of a regulatory element, such as an enhancer, with respect to a heterologous gene placed under its control reflects its natural position relative to the structural gene it naturally regulates.

Cyclin-encoding nucleic acids utilized in the present invention include nucleic acids encoding mitotic cyclins such as, for example, cyclin B; nucleic acids encoding S-phase cyclins such as, for example cyclin A, and nucleic acids encoding G1 phase cyclins. Specific cyclins which can be utilized herein include cyc1aAt, cyc3aAt, cyc3bAt, cycd1, cycd2 and the like. Preferably, the nucleic acid used in the method of the invention encodes the cyc1aAt protein (Genebank Accession No. X62279).

Genetically modified plants of the present invention are produced by contacting a plant cell with a nucleic acid sequence encoding the desired cyclin. To be effective once introduced into plant cells, the cyclin-encoding nucleic acid must be operably associated with a promoter which is effective in plant cells to cause transcription of the cyclin transgene. Additionally, a polyadenylation sequence or transcription control sequence, also recognized in plant cells, may also be employed. It is preferred that the nucleic acid be introduced via a vector and that the vector harboring the nucleic acid sequence also contain one or more selectable marker genes so that the transformed cells can be selected from non-transformed cells in culture, as described herein.

The term "operably associated" refers to finctional linkage between a regulatory sequence, preferably a promoter sequence, and the cyclin-encoding nucleic acid sequence regulated by the promoter. The operably linked promoter controls the expression of the cyclin nucleic acid sequence.

The expression of cyclin genes employed in the present invention may be driven by a number of promoters. Although the endogenous, or native promoter of a structural gene of interest may be utilized for transcriptional regulation of the gene, preferably, the promoter is a foreign regulatory sequence.

When it is desired to increase growth and yield in the whole plant, cyclin expression should be directed to all cells in the plant which are capable of dividing. This can be accomplished by using a promoter active in all meristems. Such promoters include, for example, the cdc2a promoter and the cyc07 promoter. (See for example, Ito et al., *Plant Mol. Biol.*, 24:863, 1994; Martinez et al., *Proc. Natl. Acad. Sci. USA*, 89:7360, 1992; Medford et al., *Plant Cell*, 3:359, 1991; Terada et al., *Plant Journal*, 3:241, 1993; Wissenbach et al., *Plant Journal*, 4:411, 1993).

When it is desired to increase growth and yield in a specific organ, cyclin expression should be targeted to the appropriate meristem, e.g., the shoot meristem, the floral meristem, the root meristem etc. This can be accomplished by using a tissue specific promoter. Examples of tissue specific promoters active in shoot meristems are described in Atanassova et al., *Plant Journal*, 2:291, 1992 and Medford et al., *Plant Cell*, 3:359, 1991. Examples of tissue specific promoters active in floral meristems are the promoters of the agamous and apetala 1 genes are described in Bowman et al., *Plant Cell*, 3:749, 1991; and Mandel et al., *Nature*, 360:273, 1992.

The particular promoter selected should be capable of causing sufficient cyclin expression to cause increased yield and/or increased biomass. It should be understood that cyclin expression can be altered in cells that are competent to divide. The promoters used in the vector constructs of the present invention may be modified, if desired, to affect their control characteristics.

Optionally, a selectable marker may be associated with the cyclin-encoding nucleic acid. As used herein, the term "marker" refers to a gene encoding a trait or a phenotype which permits the selection of, or the screening for, a plant or plant cell containing the marker. Preferably, the marker gene is an antibiotic resistance gene whereby the appropriate antibiotic can be used to select for transformed cells from among cells that are not transformed. Examples of suitable selectable markers include adenosine deaminase, dihydrofolate reductase, hygromycin-B-phosphotransferase, thymidine kinase, xanthine-guanine phospho-ribosyltransferase and amino-glycoside 3'-O-phosphotransferase II. Other suitable markers will be known to those of skill in the art.

To commence a transformation process in accordance with the present invention, it is first necessary to construct a suitable vector and properly introduce it into the plant cell.

Vector(s) employed in the present invention for transformation of a plant cell include a cyclin-encoding nucleic acid sequence operably associated with a promoter. Details of the construction of vectors utilized herein are known to those skilled in the art of plant genetic engineering.

Cyclin-encoding nucleic acid sequences utilized in the present invention can be introduced into plant cells using Ti plasmids of *Agrobacterium tumefaciens* (*A. tumefaciens*), root-inducing (Ri) plasmids of *Agrobacterium rhizogenes* (*A. rhizogenes*), and plant virus vectors. (For reviews of such techniques see, for example, Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7–9, and Horsch et al., *Science*, 227:1229, 1985, both incorporated herein by reference). In addition to plant transformation vectors derived from the Ti or Ri plasmids of Agrobacterium, alternative methods may involve, for example, the use of liposomes, electroporation, chemicals that increase free DNA uptake, transformation using viruses or pollen and the use of microprojection.

One of skill in the art will be able to select an appropriate vector for introducing the cyclin-encoding nucleic acid sequence in a relatively intact state. Thus, any vector which will produce a plant carrying the introduced cyclin-encoding nucleic acid should be sufficient. Even use of a naked piece of DNA would be expected to confer the properties of this invention, though at low efficiency. The selection of the vector, or whether to use a vector, is typically guided by the method of transformation selected.

The transformation of plants in accordance with the invention may be carried out in essentially any of the various ways known to those skilled in the art of plant molecular biology. (See, for example, Methods of Enzymology, Vol. 153, 1987, Wu and Grossman, Eds., Academic Press, incorporated herein by reference). As used herein, the term "transformation" means alteration of the genotype of a host plant by the introduction of cyclin-nucleic acid sequence.

For example, a cyclin-encoding nucleic acid can be introduced into a plant cell utilizing *A. tumefaciens* containing the Ti plasmid, as mentioned briefly above. In using an *A. tumefaciens* culture as a transformation vehicle, it is most advantageous to use a non-oncogenic strain of Agrobacterium as the vector carrier so that normal non-oncogenic differentiation of the transformed tissues is possible. It is also preferred that the Agrobacterium harbor a binary Ti plasmid system. Such a binary system comprises 1) a first Ti plasmid having a virulence region essential for the introduction of transfer DNA (T-DNA) into plants, and 2) a chimeric plasmid. The chimeric plasmid contains at least one border region of the T-DNA region of a wild-type Ti plasmid flanking the nucleic acid to be transferred. Binary Ti plasmid systems have been shown effective in the transformation of plant cells (De Framond, *Biotechnology*, 1:262, 1983; Hoekema et al., *Nature*, 303:179, 1983). Such a binary system is preferred because it does not require integration into the Ti plasmid of *A. tumefaciens*, which is an older methodology.

Methods involving the use of Agrobacterium in transformation according to the present invention include, but are not limited to: 1) co-cultivation of Agrobacterium with cultured isolated protoplasts; 2) transformation of plant cells or tissues with Agrobacterium; or 3) transformation of seeds, apices or meristems with Agrobacterium.

In addition, gene transfer can be accomplished by in planta transformation by Agrobacterium, as described by Bechtold et al., (*C.R. Acad. Sci. Paris*, 316:1194, 1993) and exemplified in the Examples herein. This approach is based on the vacuum infiltration of a suspension of Agrobacterium cells.

The preferred method of introducing a cyclin-encoding nucleic acid into plant cells is to infect such plant cells, an explant, a meristem or a seed, with transformed *A. tumefaciens* as described above. Under appropriate conditions known in the art, the transformed plant cells are grown to form shoots, roots, and develop further into plants.

Alternatively, cyclin-encoding nucleic acid can be introduced into a plant cell using mechanical or chemical means. For example, the nucleic acid can be mechanically transferred into the plant cell by microinjection using a micropipette. Alternatively, the nucleic acid may be transferred into the plant cell by using polyethylene glycol which forms a precipitation complex with genetic material that is taken up by the cell.

Cyclin-encoding nucleic acid can also be introduced into plant cells by electroporation (Fromm et al., *Proc. Natl. Acad. Sci., USA.*, 82:5824, 1985, which is incorporated herein by reference). In this technique, plant protoplasts are electroporated in the presence of vectors or nucleic acids containing the relevant nucleic acid sequences. Electrical impulses of high field strength reversibly permeabilize membranes allowing the introduction of nucleic acids. Electroporated plant protoplasts reform the cell wall, divide and form a plant callus. Selection of the transformed plant cells with the transformed gene can be accomplished using phenotypic markers as described herein.

Another method for introducing a cyclin-encoding nucleic acid into a plant cell is high velocity ballistic penetration by small particles with the nucleic acid to be introduced contained either within the matrix of such particles, or on the surface thereof (Klein et al., *Nature* 327:70, 1987). Bombardment transformation methods are also described in Sanford et al. (*Techniques* 3:3–16, 1991) and Klein et al. (*Bio/Techniques* 10:286, 1992). Although, typically only a single introduction of a new nucleic acid sequence is required, this method particularly provides for multiple introductions.

Cauliflower mosaic virus (CaMV) may also be used as a vector for introducing nucleic acid into plant cells (U.S. Pat. No. 4,407,956). CaMV viral DNA genome is inserted into a parent bacterial plasmid creating a recombinant DNA molecule which can be propagated in bacteria. After cloning, the recombinant plasmid again may be cloned and further modified by introduction of the desired nucleic acid sequence. The modified viral portion of the recombinant plasmid is then excised from the parent bacterial plasmid, and used to inoculate the plant cells or plants.

As used herein, the term "contacting" refers to any means of introducing a cyclin-encoding nucleic acid into a plant cell, including chemical and physical means as described above. Preferably, contacting refers to introducing the nucleic acid or vector containing the nucleic acid into plant cells (including an explant, a meristem or a seed), via *A. tumefaciens* transformed with the cyclin-encoding nucleic acid as described above.

Normally, a plant cell is regenerated to obtain a whole plant from the transformation process. The immediate product of the transformation is referred to as a "transgenote". The term "growing" or "regeneration" as used herein means growing a whole plant from a plant cell, a group of plant cells, a plant part (including seeds), or a plant piece (e.g., from a protoplast, callus, or tissue part).

Regeneration from protoplasts varies from species to species of plants, but generally a suspension of protoplasts is first made. In certain species, embryo formation can then be induced from the protoplast suspension. The culture media will generally contain various amino acids and hormones, necessary for growth and regeneration. Examples of hormones utilized include auxins and cytokinins. Efficient regeneration will depend on the medium, on the genotype, and on the history of the culture. If these variables are controlled, regeneration is reproducible.

Regeneration also occurs from plant callus, explants, organs or parts. Transformation can be performed in the context of organ or plant part regeneration. (see *Methods in Enzymology*, Vol. 118 and Klee et al., *Annual Review of Plant Physiology*, 38:467, 1987). Utilizing the leaf disk-transformation-regeneration method of Horsch et al., *Science*, 227:1229, 1985, disks are cultured on selective media, followed by shoot formation in about 2–4 weeks. Shoots that develop are excised from calli and transplanted to appropriate root-inducing selective medium. Rooted plantlets are transplanted to soil as soon as possible after roots appear. The plantlets can be repotted as required, until reaching maturity.

In vegetatively propagated crops, the mature transgenic plants are propagated by utilizing cuttings or tissue culture techniques to produce multiple identical plants. Selection of desirable transgenotes is made and new varieties are obtained and propagated vegetatively for commercial use.

In seed propagated crops, mature transgenic plants can be self crossed to produce a homozygous inbred plant. The resulting inbred plant produces seed containing the newly introduced foreign gene(s). These seeds can be grown to produce plants that would produce the selected phenotype, e.g. increased yield.

Parts obtained from regenerated plant, such as flowers, seeds, leaves, branches, roots, fruit, and the like are included in the invention, provided that these parts comprise plant cells that have been transformed as described. Progeny and variants, and mutants of the regenerated plants are also included within the scope of the invention, provided that these parts comprise the introduced nucleic acid sequences.

Plants exhibiting increased growth and/or yield as compared with wild-type plants can be selected by visual observation. The invention includes plants produced by the method of the invention, as well as plant tissue and seeds.

In another embodiment, the invention provides a method of producing a plant characterized as having increased growth and yield by contacting a plant capable of increased yield with a cyclin promoter-inducing amount of an agent which induces cyclin gene expression. Induction of cyclin gene expression results in production of a plant having increased yield as compared to a plant not contacted with the agent.

A "plant capable of increased yield" refers to a plant that can be induced to express its endogenous cyclin gene to achieve increased yield. The term "promoter inducing amount" refers to that amount of an agent necessary to elevate cyclin gene expression above cyclin expression in a plant cell not contacted with the agent, by stimulating the endogenous cyclin promoter. For example, a transcription factor or a chemical agent may be used to elevate gene expression from native cyclin promoter, thus inducing the promoter and cyclin gene expression.

The invention also provides a method of providing increased transcription of a nucleic acid sequence in a selected tissue. The method comprises growing a plant having integrated in its genome a nucleic acid construct comprising, an exogeneous gene encoding a cyclin protein, said gene operably associated with a tissue specific whereby transcription of said gene is increased in said selected tissue.

Plant development is plastic with post-embryonic organogenesis mediated by meristems (Steeves and Sussex, *Patterns in Plant Development*, 1–388 (Press Syndicate of the University of Cambridge, Cambridge, 1989)). Although cell division is intrinsic to meristem initiation, maintenance and proliferative growth, the role of the cell cycle in regulating growth and development is unclear. To address this question, the expression of cdc2 and cyclin genes, which encode the catalytic and regulatory subunits, respectively, of cyclin-dependent protein kinases controlling cell cycle progression (Murray and Hunt, *The Cell Cycle* (New York), 1993) were examined. Unlike cdc2, which is expressed not only in apical meristems but also in quiescent meristems, (Martinez et al., *Proc. Natl. Acad. Sci. USA*, 89:7360, 1992), transcripts of cyc1aAt accumulated specifically in active meristems and dividing cells immediately before cytokinesis. Ectopic expression of cyc1aAt under control of the cdc2aAt promoter in Arabidopsis plants markedly accelerated growth without altering the pattern of development or inducing neoplasia. Thus, cyclin expression is a limiting factor for growth.

The above disclosure generally describes the present invention. A more complete understanding can be obtained by reference to the following specific examples which are provided herein for purposes of illustration only and are not intended to limit the scope of the invention.

EXAMPLE 1

A full length cyc1aAt cyclin cDNA was placed under control of the Arabidopsis cdc2aAt promoter (Hemerly et al., 1992, supra). The chimeric gene was cloned into a T-DNA transformation vector carrying the selection marker hygromycin phospho-transferase (Hyg$^r$) and transformed into Arabidopsis using the vacuum-infiltration method (Bechtold and Pelletier, *Acad. Sci. Paris, Life Sci.*, 316:1194, 1993) to introduce *Agrobacterium tumefaciens*. Several independent transgenic lines having elevated steady-state levels of cyc1aAt mRNA showed a dramatic increase of both main and lateral root growth rate, correlated with proportionally increased fresh weight, dry mass and DNA content, but not cell size. Enhanced growth was orderly, with no observed differences in morphology and clearly not neoplastic.

Arabidopsis seedlings (ecotype Columbia) were grown in 20 ml MS medium (Murashige and Skoog, *Physiol. Plant.*, 15:473, 1962). Eight- to 10-day-old plants were transferred to MS medium buffered with 50 mM potassium phosphate, pH 5.5, and initiation of lateral roots was stimulated by addition of IAA to 10 $\mu M_{eff}$ (non-dissociated IAA). Roots were collected at the time points indicated and total RNA and protein isolated. 500 ng poly(A)+RNA was separated on 1% formaldehyde gels (Ausubel et al., *Current Protocols in Molecular Biology*, Green Publishing Associates and Wiley-Interscience, New York, 1987), transferred to Nytran membranes (Schleicher and Schüll) and hybridized to $^{32}$P-labeled probes corresponding to nucleotides (nt) 674–1004 of cyc1aAt (Hemerly et al., *Proc. Natl. Acad. Sci. USA*, 89:3295, 1992), or nt 661–1386 of Arabidopsis cdc2aAt (Hirayama et al., *Gene*, 105:159, 1991), followed by hybridization with nt 2576–2824 of Arabidopsis UBQ3 (Norris etal., *Plant Mol. Biol.*, 21:895, 1993) for normalization. Blots were quantified with a Molecular Dynamics Phosphorimager. cyc1aAt is a single copy gene in Arabidopsis. Total protein was separated on 12% SDS-PAGE and transferred to PVDF membranes. $p34^{cdc2aAt}$ was detected with serum raised in rabbits against the peptide YFKDLGGMP (SEQ ID NO:1), corresponding to amino acids 286–294, and visualized by Enhanced Chemiluminescence Assay (Amersham).

Figure 1B:
Figure 1C:
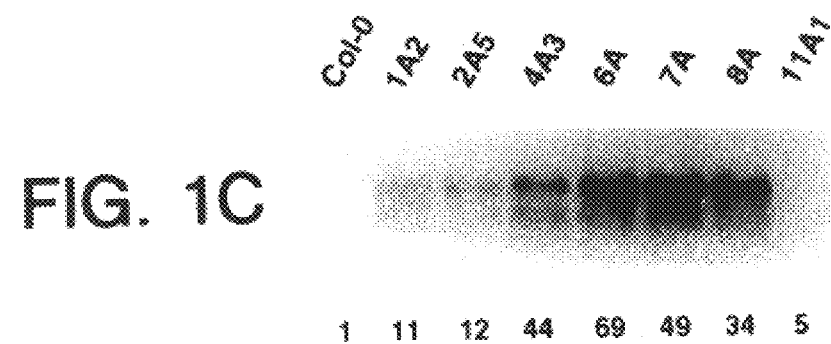
Figure 2A:
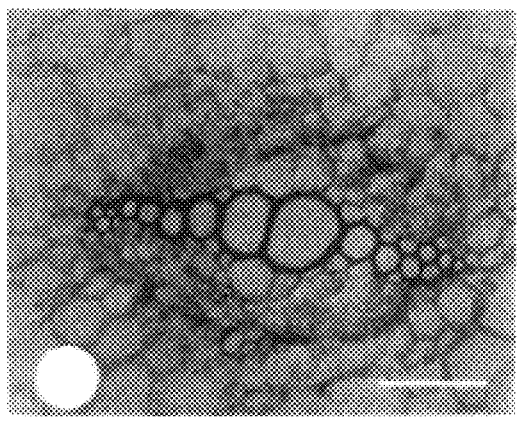
FIG. 2 shows an in situ hybridization analysis of cdc2aAt and cyc1aAt transcripts in root apices and developing lateral roots. Panels a–d show cross sections of quiescent roots (panels a,b) or proliferating cells in primordia (panels c,d) that were hybridized to cdc2aAt (a) or cyc1aAt (b–d) anti-sense probes. Panels e, f show cyc1aAt mRNA abundance in contiguous meristematic cell files in root apices. Transcript accumulation is indicated by silver grain deposition and visualized by indirect red illumination. Scale bar is 10 $\mu$m in a–d, 5 $\mu$m in e. fc, founder cell accumulating cyc1aAt transcripts; p, pericycle cell layer; r, towards the root apex; s, towards the shoot.
Figure 2B:
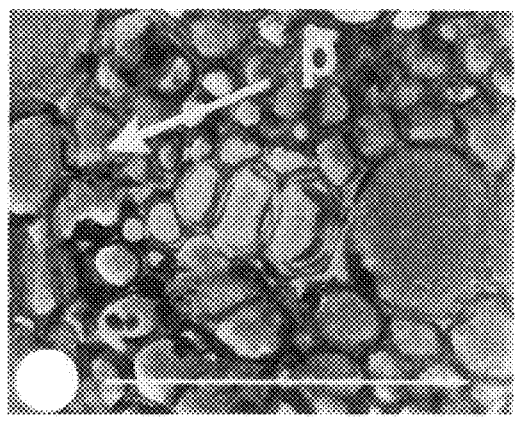
Figure 2C:
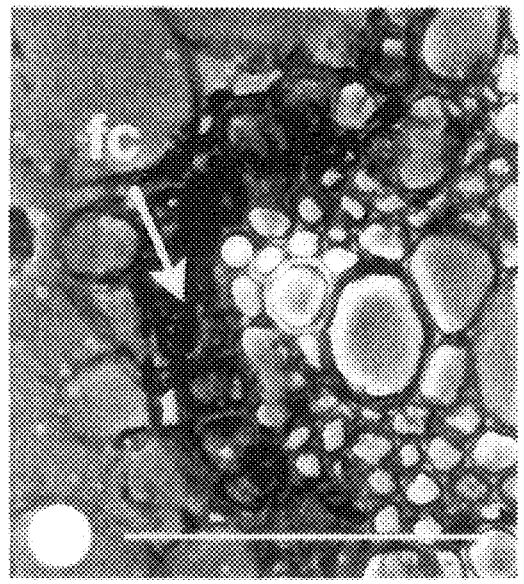
Figure 2D:
Figure 2E:
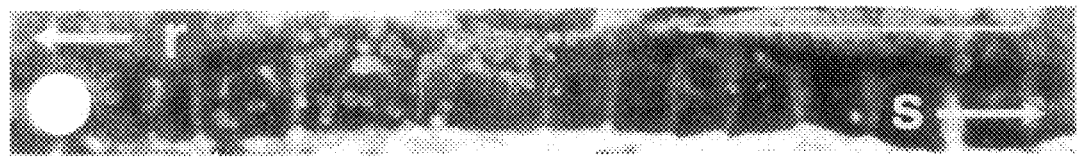
Figure 2F:
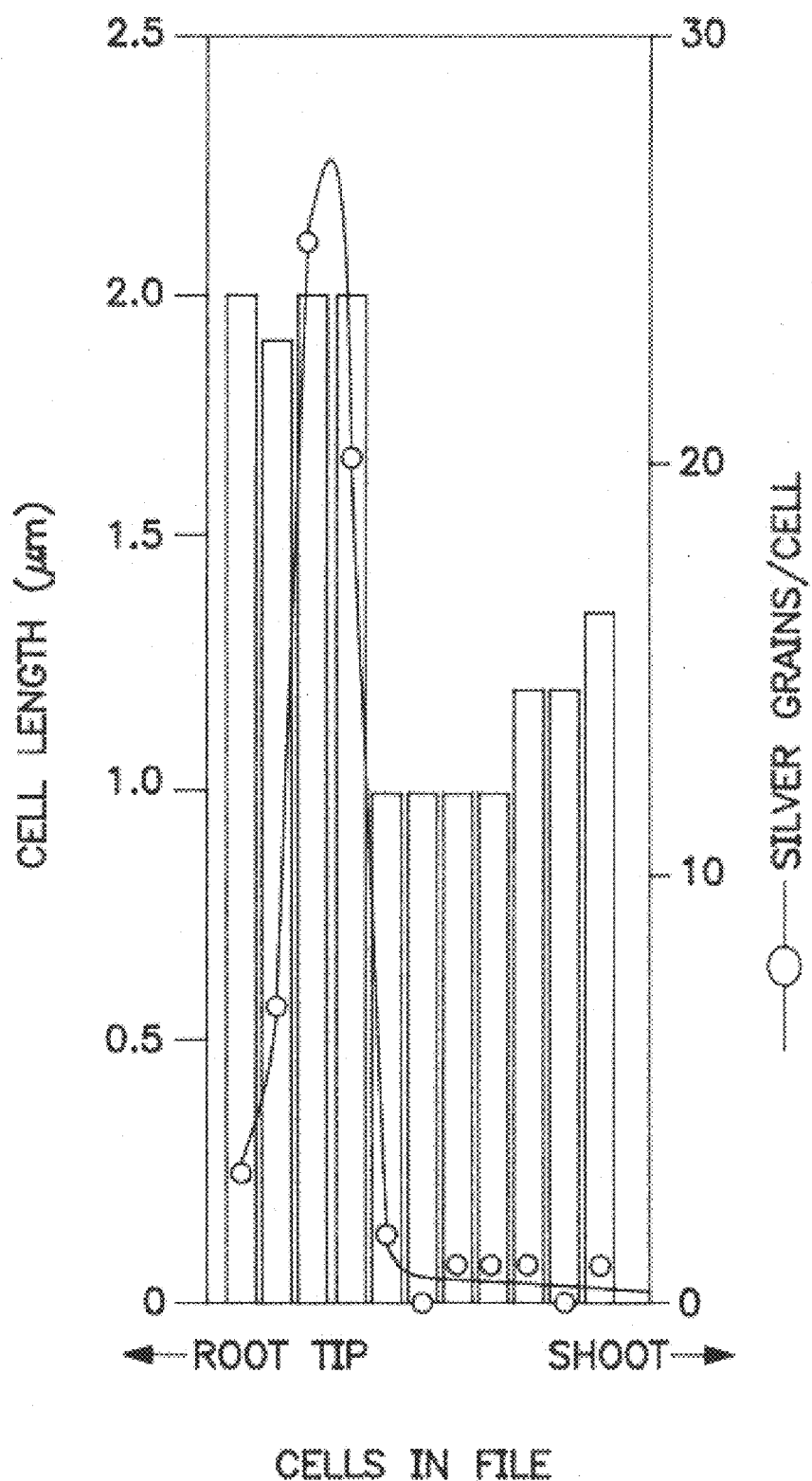

FIG. 1 shows steady state levels of cdc2aAt mRNA and p34 protein, panel a; cyc1aAt mRNA during IAA induction of lateral root meristems, panel b; cyc1aAt mRNA in selected non-induced transgenic lines, panel c; normalized transcript levels relative to wild-type are indicated. Col-0, wild-type; 1A2, 2A5, 4A3, 11A1: T2 homozygous; 6A, 7A, 8A: T1 heterozygous transgenic lines. cyc1aAt mRNA levels in the lines 4A3, 6A, 7A, 8A, and 3A exceeded those of IAA induced wild-type roots.

The levels of cdc2 mRNA and $p34^{cdc2}$ protein per cell did not markedly change following stimulation of lateral root initiation by the auxin indoleacetic acid (IAA) (FIG. 1, panel a). Hence, while cdc2 expression is correlated with the competence to divide, root growth and initiation of lateral roots do not appear to be limited by the abundance of the cyclin-dependent protein kinase p34 catalytic subunit and, moreover, ectopic expression of cdc2 in transgenic Arabidopsis failed to perturb growth or development (Hemerly et al., *EMBO J.*, 14:3925, 1995).

In contrast, IAA treatment of Arabidopsis roots induced the expression of several cyc genes from low basal levels and in particular cyc1aAt mRNA, which encodes a mitotic cyclin (Hemerly et al., supra)), exhibited a rapid 15 to 20-fold increase (FIG. 1, panel b).

FIG. 2 shows an in situ hybridization analysis of cdc2aAt and cyc1aAt transcripts in root apices and developing lateral roots. Panels a–d show cross sections of quiescent roots (panels a,b) or proliferating cells in primordia (panels c,d) that were hybridized to cdc2aAt (a) or cyc1aAt (b–d) anti-sense probes. Panels e,f show cyc1aAt mRNA abundance in contiguous meristematic cell files in root apices. Transcript accumulation is indicated by silver grain deposition and visualized by indirect red illumination. Scale bar is 10 μm in a–d, 5 μm in e. fc, founder cell accumulating cyc1aAt transcripts; p, pericycle cell layer; r, towards the root apex; s, towards the shoot.

Tissue samples were processed for in situ hybridization to examine expression of cyclin transcripts. The samples were treated with 10 μM IAA. After 8 or 24 h incubation, radish (*Raphanus sativa* var Scarlet Globe) roots were processed as described (Drews et al., *Cell*, 65:991, 1991). Sections (8 μm) were hybridized to a $^{33}$P-labeled RNA probe, corresponding to nt 674–1004 of cyc1aAt(Hemerly et al., supra) (FIG. 2, panels b–e) or to a $^{35}$S-labeled probe used in a corresponding to nt 661–1386 of cdc2aAt (Hirayama et al., supra), for 14 h at 48° C. in 50% formamide. After hybridization, the final washes were for 1 h at 58° C. in 0.015 m NaCl and slides were then exposed for 3 weeks (cyc1aAt) or 5 d (cdc2aAt). After developing, silver grains were illuminated laterally with red light, specimens were visualized by phase contrast and double exposures were taken on FUJI Velvia film. Images were assembled in ADOBE Photoshop. For the analysis summarized in FIG. 2, panel f, silver grains were counted and cell size measured in the cell file shown in FIG. 2, panel e.

In situ hybridization showed that, unlike cdc2, cyc1aAt transcripts were not detected in quiescent pericycle cells, but accumulated in single, cytoplasmically dense cells of incipient lateral root primordia, and in the emergent organ cyc1aAt was expressed exclusively in the meristem (FIG. 2, panels a–d). Moreover, crucifer roots consisted of long cell files that arise by transverse divisions followed by longitudinal expansion (Dolan et al., *Development*, 119:71, 1993), and within such a contiguous spatial display of sequential cell division phases, cyc1aAt transcripts accumulated only in large cells immediately prior to cytokinesis, declining to background levels in the adjacent small daughter cells (FIG. 2, panels e, f). A similar, stringent spatio-temporal relationship of cyclin expression and mitosis was observed in Antirrhinum shoot apical meristems (Fobert et al., *EMBO J.*, 13:616, 1994).

The close correlation between cyc1aAt expression and cell division during growth of the root apical meristem and the initiation of lateral roots, together with the pattern of cyc1aAt promoter activity deduced from the expression of cyc1aAt::uidA gene fusions in transgenic Arabidopsis (Ferreira et al., *Plant Cell*, 6:1763, 1994), suggested that cyclin abundance might be a key factor regulating root growth and development. To test this hypothesis transgenic Arabidopsis were generated (Bechtold and Pelletier, *Acad. Sci. Paris, Life Sci.*, 316:1194, 1993) containing cyc1aAt under control of the cdc2aAt promoter. Five transformants were obtained in which the level of cyc1aAt mRNA in untreated roots exceeded that observed in IAA-stimulated roots of wild-type plants (FIG. 1, panel c), and these lines were chosen for further study.

An NheI site was introduced in the third codon of the cyc1aAt cDNA by in vitro mutagenesis and this open reading frame subsequently ligated to the cdc2aAt promoter with an in vitro generated XbaI site at codon 3. This fragment was ligated into pBiB-Hyg (Becker et al., *Pl. Mol. Biol.*, 20:1195, 1992) and transfected into *Agrobacterium tumefaciens* GV3101 (Koncz and Schell, *Mol. Gen. Genet.*, 204:383, 1986). *Arabidopsis thaliana* (*A. thaliana*) (ecotype Columbia) was transformed by vacuum infiltration (Bechtold et al., supra), and transgenic seedlings (T0 generation) were selected on MS plates containing 30 μg/ml hygromycin. 52 independent transgenic lines were obtained and elevated levels of cyc1aAt mRNA were detected in 9 of the 11 lines analyzed in detail. Growth assays were performed on heterozygous T1 and homozygous T2 progeny as indicated.

Figure 3A:
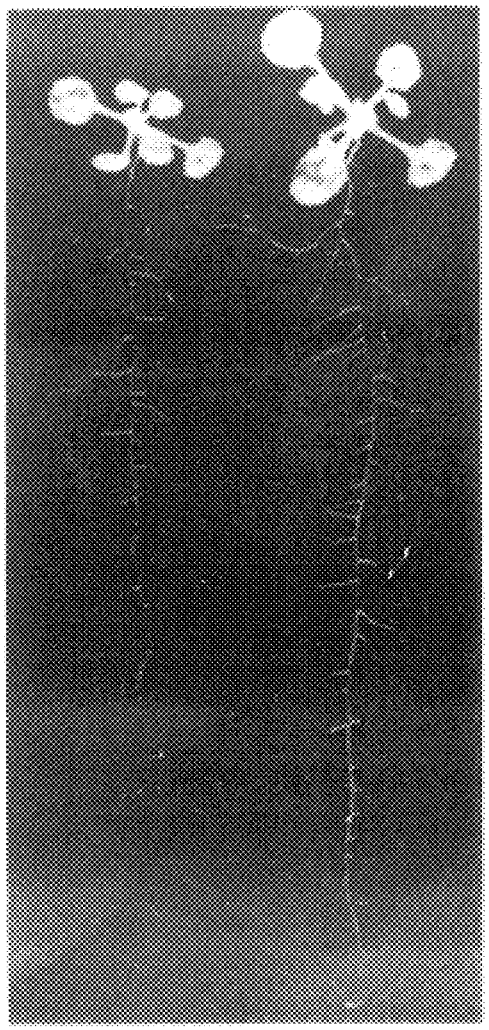
FIG. 3 shows increased root growth rate in *Arabidopsis thaliana* (*A. thaliana*) ectopically expressing cyc1aAt cyclin. Panel a, Wild-type (left) or transgenic line 6A (T1 generation) containing the cdc2aAt::cyc1aAt gene fusion (right). Arabidopsis seed were plated on MS (3% sucrose) agar and grown in a vertical orientation for 7 d. Plants transformed with the vector alone or with unrelated promoter::uidA constructs or with a cdc2aAt::cyc1aAt fusion in which the cdc2aAt 5' untranslated leader was interrupted by a DS transposon insertion did not show this phenotype. Panel b, wild-type (left) or transgenic line 6A (T1 generation) (right) 6 d after IAA induction of lateral roots. One week-old seedlings grown hydroponically were treated with 10 $\mu$M IAA$_{eff}$ to stimulate lateral root development.
Figure 3B:
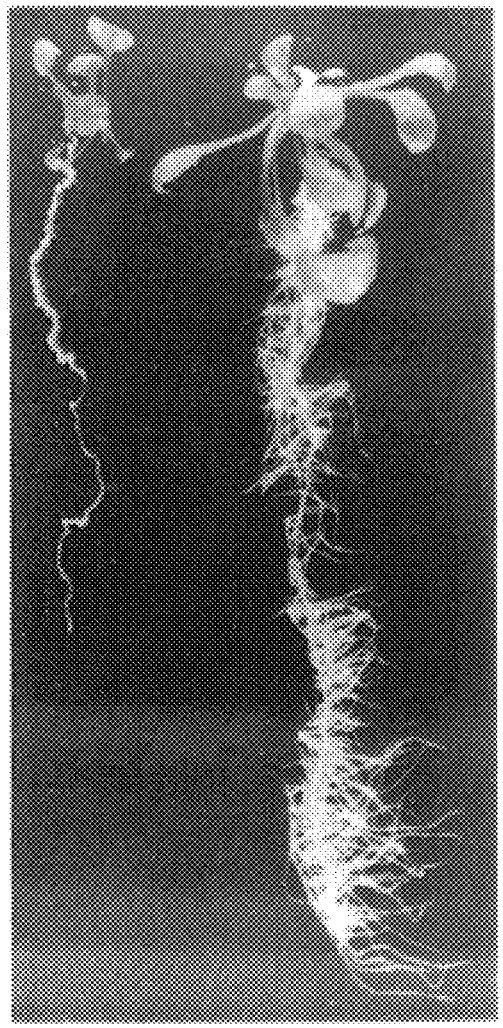

FIG. 3 shows increased root growth rate in Arabidopsis ectopically expressing cyc1aAt cyclin. Panel a, Wild-type (left) or transgenic line 6A (T1 generation) containing the cdc2aAt::cyc1aAt gene fusion (right). Arabidopsis seed were plated on MS (3% sucrose) agar and grown in a vertical orientation for 7 d. Plants transformed with the vector alone or with unrelated promoter::uidA constructs or with a cdc2aAt::cyc1aAt fusion in which the cdc2aAt 5' untranslated leader was interrupted by a DS transposon insertion did not show this phenotype. Panel b, wild-type (left) or transgenic line 6A (T1 generation) (right) 6 d after IAA induction of lateral roots. One week-old seedlings grown hydroponically were treated with 10 μM $IAA_{eff}$ to stimulate lateral root development.

Strong expression of the cdc2aAt::cyc1aAt transgene caused a marked increase in the rate of organized root growth (FIG. 3, panel a). Homozygous or heterozygous seed were plated on MS agar and plants grown in vertical orientation for 7 days with a 16 h day/8 h night schedule at 22° C. Four images of each plate were acquired with a Speedlight Platinum frame grabber (Lighttools Research) at 24 h intervals and root growth analyzed with NIH-Image by measuring the displacement of root apices. Following growth analysis, roots from 10 plants of each class were collected and RNA analyzed. To measure cell sizes, roots were cleared by overnight incubation in saturated chloral hydrate, visualized with Normarski optics, photographed and analyzed with NIH-Image. Statistical analysis (t-test with unpaired variances) was performed with MS Excel. Root growth in IAA-treated plants was assessed 3 and 6 d after induction by determination of fresh weight of roots excised from liquid-grown plants and then dry weight following lyophilization for 24 h. Total DNA was extracted from dried material (Ausubel et al., supra).

In heterozygous T2 progeny, increased growth rate, measured by displacement of the apex of the main root in time-lapse photography, strictly co-segregated with transgene expression and individuals lacking the transgene grew at the same rate as wild-type plants (Table 1). The average size of epidermal, cortical, endodermal and pericycle cells was equivalent or slightly reduced in cdc2aAt::cyc1aAt transformants compared to wild-type plants (Table 2), and hence increased growth reflects increased cell number rather than cell size. The pattern of spontaneous lateral root initiation and overall root morphology were indistinguishable in wild-type and transgenic plants (FIG. 3, panel a). When treated with 1 $\mu$M IAA, which induces well-separated lateral root primordia, the frequency of primordia initiated per unit length of the main roots was not altered (mean of 1.08 initials/mm with a standard deviation of 0.09 in wild-type compared with 1.14+/−0.07 and 1.09+/−0.13 in the two transgenic lines examined). However, growth and development of lateral roots following induction by 10 $\mu$M IAA, was markedly accelerated in the cdc2aAt::cyc1aAt transformants, giving rise to a much enlarged root system (FIG. 3, panel b). Enhanced root growth in cdc2aAt::cyc1aAt plants following IAA treatment superficially resembles the alf1 phenotype (Celenza et al., Genes & Development, 9:2131, 1995) and these plants have elevated levels of cyc1aAt transcripts but in contrast to cdc2aAt::cyc1aAt transformants, alf1 plants initiate supernumerary lateral roots. The several-fold greater gain of fresh weight in IAA-treated cdc2aAt::cyc1aAt plants compared to equivalent wild-type controls was accompanied by marked increased in DNA content and dry weight (Table 3). Confocal microscopy confirmed that the enhanced growth response to IAA, which was also observed in several lines showing weaker cdc2aAt::cyc1aAt expression, did not reflect transgene stimulation of cell vacuolation or elongation. Thus, ectopic cyclin expression enhances root growth by stimulation of cell division activity in meristems, thereby increasing the rate of cell production without altering meristem organization.

The data above indicate that cdc2aAt::cyc1aAt expression is sufficient to enhance growth from established apical meristems, suggesting that cell cycle activity regulates meristem activity. However, the failure to induce gratuitous organ primordia by ectopic expression of cyc1aAt under control of the cdc2aAt promoter implies additional control points in the generation of a new apical meristem, either through post-translational regulation of cyclin-dependent protein kinase activity or the operation of parallel regulatory pathways. In most animal cells, the commitment to cell division occurs late in G1 (Pardee, A. B., Science, 246:603, 1989), and cyclin D1 and cyclin E are rate-limiting for G1 progression in cultured cells (Ohtsubo and Roberts, Science, 259:1908, 1993; Quelle et al., Genes Dev., 7:1559, 1993; Resnitzky and Reed, Mol. Cell Biol., 15:3463, 1995). Elevated levels of cyclin D1 are observed in several tumors (Motokura et al., Nature, 350:512, 1991; Rosenberg et al., Proc. Natl. Acad. Sci. USA, 88:9638, 1991; Withers et al., Mol. Cell Biol., 11:4864, 1991) and ectopic expression in transgenic mice promotes hyperplasia and adenocarcinomas (Wang et al., Nature, 369:669, 1994).

In contrast, ectopic expression of cyc1aAt did not result in neoplasia but stimulated organized growth, without altering meristem organization or size as monitored by confocal microscopy. Moreover, morphology of the transgenic plants was not altered and increased growth was accompanied by accelerated organ development. Thus, cyclin expression is a crucial, limiting upstream factor in an intrinsic regulatory hierarchy governing meristem activity, organized growth and indeterminate plant development. This regulatory hierarchy, which is distinctly different from that in animals, where determinate development limits proliferative growth, exemplified by the strict morphogenetic control of cell division during muscle differentiation (Halevy et al., Science, 267:1018, 1995; Skapek et al., Science, 267:1022, 1995), may underlie the striking plasticity of plant growth and development (Drew, M. C., New Phytol., 75:479, 1975). Cyclin abundance may function as a rheostat to allow flexible growth control in response to changes in the environment such as nutrient availability.

TABLE 1

Root apical growth

| Plant line | | Rate [$\mu$m · h$^{-1}$] | % of wild-type | n |
|---|---|---|---|---|
| Col-O | (−) | 254.1 | 100 | 57 |
| 2A5 | (−) | 253.1 | 99.6 | 56 |
| 3A | (+) | 341.4* | 134.4 | 20 |
| 3A | (−) | 259.4 | 102.1 | 30 |
| 4A3 | (+) | 291.6* | 114.8 | 47 |
| 6A | (+) | 354.1* | 139.5 | 20 |
| 6A | (−) | 252.4 | 99.3 | 16 |
| 7A | (+) | 344.9* | 135.7 | 24 |
| 7A | (−) | 249.8 | 98.3 | 19 |
| 8A | (+) | 335.4* | 131.9 | 21 |
| 8A | (−) | 258.6 | 101.8 | 31 |
| 11A1 | (−) | 258.8 | 101.8 | 45 |
| 2A5 | (−) | 253.1 | 99.6 | 56 |

Table 1 shows a comparison of root apical growth rates. Plant line = independent transformants (except for Col-O). (+) = plants that show enhanced growth phenotype due to presence of adequate levels of cyclin-encoding nucleic acid. (−) = plants that have lost introduced cyclin-encoding nucleic acid or do not exhibit sufficient cyclin expression for enhanced growth. Rate = rate of displacement of root apex per unit time. (*denotes values significantly different from Wild-Type growth rate.) n = number of individual plants analyzed.

TABLE 2

| | Plant line | | | | | |
|---|---|---|---|---|---|---|
| | Col-O (wild type) | | 7A (transgenic) | | 8A (transgenic) | |
| Cell Type | Size [$\mu$m] | n | Size [$\mu$m] | n | Size [$\mu$m] | n |
| Epidermis | 137 | 37 | 129 | 34 | 158 | 12 |
| Cortex | 159 | 31 | 135* | 7 | 160 | 9 |
| Endodermis | 109 | 23 | 90* | 22 | 107 | 11 |
| Pericycle | 73 | 26 | 67 | 19 | 71 | 57 |

TABLE 3

Growth of seedling root system

| Plant line | Fresh weight [mg] | | Dry weight [mg] | | DNA per root [µg] | |
|---|---|---|---|---|---|---|
| | 3d | 6d | 3d | 6d | 3d | 6d |
| Col-O | 11 | 25 | 1.7 | 2.4 | 5 | 14 |
| 4A3 | 31 | 136 | 4.5 | 15.4 | 8 | 35 |
| 6A | 30 | 155 | 4.2 | 19.3 | 10 | 46 |
| 7A | 24 | 156 | 3.5 | 16.8 | 9 | 38 |
| 8A | 18 | 134 | 2.5 | 12.8 | 8 | 33 |

Table 2 shows a comparison of cell size; and Table 3 shows a comparison of root growth after 1AA treatment in wild-type and in transgenic Arabidopsis lines containing the cdc2aAt::cyclaAt gene fusion. The lines 3A, 6A, 7A, 8A are heterozygous T1 populations with more than one introduced transgene; (+) denotes plants with increased cyclaAt transcript levels, (−) plants with wild-type cyclaAt transcript levels. The following T2 lines are homozygous for cdc2aAt::cyclaAt: 2A5, 4A3 and 11A1; constitutive cyclaAt expression in 4A3, but not in 2A5 and 11A1, exceeds 1AA-induced wild-type levels (Fig. 1). n, number of plants analyzed. *, means that are significantly different from the wild-type; for a, $P < 0.001$, for b, $P < 0.01$. Fresh weight = weight of freshly excised root system. Dry weight = weight after 24 hours of drying.

The foregoing description of the invention is exemplary for purposes of illustration and explanation. It should be understood that various modifications can be made without departing from the spirit and scope of the invention. Accordingly, the following claims are intended to be interpreted to embrace all such modifications.

What is claimed is:

1. A method of producing a genetically modified plant characterized as having increased root growth and yield as compared to the corresponding wild-type plant, said method comprising:

contacting plant cells with nucleic acid encoding a cyclin protein, wherein said nucleic acid is operably associated with a regulatory sequence, to obtain transformed plant cells;

producing plants from said transformed plant cells; and selecting a plant exhibiting said increased root gowth and yield.

2. The method of claim 1, wherein the cyclin is cyc1aAt.

3. The method of claim 1, wherein the regulatory sequence is a promoter.

4. The method of claim 3, wherein the promoter is selected from the group consisting of constitutive promoters and inducible promoters.

5. The method of claim 1, wherein the contacting is by physical means.

6. The method of claim 1, wherein the contacting is by chemical means.

7. The method of claim 1, wherein the plant cell is selected from the group consisting of protoplasts, gamete producing cells, and cells which regenerate into whole plants.

8. The method of claim 1, wherein said nucleic acid is contained in a T-DNA derived vector.

9. A method of providing increased transcription of a nucleic acid sequence in plant root tissue, wherein said method comprises:

growing a plant having integrated in its genome a nucleic acid construct comprising nucleic acid encoding a cyclin protein, wherein said nucleic acid is operably associated with a tissue specific promoter whereby expression of said cyclin-encoding nucleic acid is increased in said plant root tissue.

* * * * *